(12) United States Patent
Rodriguez et al.

(10) Patent No.: US 7,383,788 B2
(45) Date of Patent: Jun. 10, 2008

(54) ENHANCED FEEDING AND GROWTH RATES OF AQUATIC ANIMALS FED AN ASTAXANTHIN PRODUCT DERIVED FROM MARIGOLD EXTRACT

(75) Inventors: Gustavo Rodriguez, Sinaloa (MX); George Schloemer, Longmont, CO (US); Victor Artola, Sinaloa (MX)

(73) Assignee: DSM IP Assets B.V., Te Heerlen (NL)

( * ) Notice: Subject to any disclaimer, the term of this patent is extended or adjusted under 35 U.S.C. 154(b) by 128 days.

(21) Appl. No.: 10/922,724

(22) PCT Filed: Mar. 11, 2003

(86) PCT No.: PCT/US03/07580

§ 371 (c)(1), (2), (4) Date: Dec. 6, 2004

(87) PCT Pub. No.: WO03/077950

PCT Pub. Date: Sep. 25, 2003

(65) Prior Publication Data

US 2006/0037543 A1 Feb. 23, 2006

Related U.S. Application Data

(60) Provisional application No. 60/363,661, filed on Mar. 11, 2002.

(51) Int. Cl.
*A01K 61/02* (2006.01)
(52) U.S. Cl. .............. 119/230; 119/51.01; 426/635
(58) Field of Classification Search ............ 119/230, 119/51.01, 51.04; 426/635
See application file for complete search history.

(56) References Cited

U.S. PATENT DOCUMENTS

| | | | | |
|---|---|---|---|---|
| 4,239,782 A | * | 12/1980 | Cinquemani | 426/2 |
| 4,871,551 A | * | 10/1989 | Spencer | 426/2 |
| 5,219,867 A | * | 6/1993 | Gollamudi et al. | 514/316 |
| 5,739,006 A | * | 4/1998 | Abe et al. | 435/67 |
| 5,744,502 A | | 4/1998 | Lignell et al. | |
| 5,959,138 A | * | 9/1999 | Torres-Cardona et al. | 560/190 |
| 6,015,684 A | * | 1/2000 | Jacobson et al. | 435/67 |
| 6,083,520 A | * | 7/2000 | Toneby | 424/420 |
| 6,083,541 A | * | 7/2000 | Hamstra et al. | 426/63 |
| 6,299,912 B1 | * | 10/2001 | Ito et al. | 426/2 |
| 6,329,557 B1 | * | 12/2001 | Rodriguez et al. | 568/834 |
| 6,376,650 B1 | * | 4/2002 | Raa et al. | 530/343 |
| 6,413,736 B1 | * | 7/2002 | Jacobson et al. | 435/67 |
| 6,509,030 B2 | * | 1/2003 | Sakiura | 424/442 |
| 6,818,239 B2 | * | 11/2004 | Kagan et al. | 426/429 |
| 6,844,020 B2 | * | 1/2005 | Johnson et al. | 426/540 |
| 6,958,385 B2 | * | 10/2005 | Raa et al. | 530/343 |

FOREIGN PATENT DOCUMENTS

| | | |
|---|---|---|
| JP | 04-053455 | 2/1992 |
| WO | WO 03/003848 | 1/2003 |

OTHER PUBLICATIONS

Christiansen, et al. "Effect of Astaxanthin and Vitamin A on Growth and Survival During First Feeding of Atlantic Salmon, *Salmo salar* L.," *Aquaculture and Fisheries Management*, vol. 25, pp. 903-914, 1994.

Vernon-Carter, et al. "Pigmentation of Pacific White Shrimp (*Penaeus vannamei*) Using Aztec Marigold (*Tagetes erecta*) Extracts As The Carotenoid Source," *Archivo Latinoamericanos de Nutrición*, vol. 46, No. 3, pp. 243-246, 1996.

Supplementary European Search Report, completed May 30, 2005 and issued to a related foreign application.

\* cited by examiner

*Primary Examiner*—Peter M. Poon
*Assistant Examiner*—Bethany L. Griles
(74) *Attorney, Agent, or Firm*—Nixon & Vanderhye, P.C.

(57) ABSTRACT

The present invention relates to the use of an astaxanthin pigment product obtained by semi-synthesis from marigold extract to substantially enhance the feeding and growth rates of commercially cultivated aquatic species when added to the feed mixture in concentrations useful in producing fish and shrimp coloration. More particularly, this product induces growth rates substantially greater than any currently available feed additive for salmon, trout and shrimp.

14 Claims, No Drawings

ENHANCED FEEDING AND GROWTH RATES OF AQUATIC ANIMALS FED AN ASTAXANTHIN PRODUCT DERIVED FROM MARIGOLD EXTRACT

RELATED APPLICATIONS

This application is the U.S. national phase under 35 U.S.C. § 371 of International Application PCT/US03/07580 filed Mar. 11, 2003, which claims priority to U.S. Provisional Application No. 60/363,661, filed Mar. 11, 2002, both of which are incorporated hereby in reference in their entirety.

BACKGROUND OF THE INVENTION

1. Field of the Invention

The present invention relates to the use of an astaxanthin pigment product obtained by semi-synthesis from marigold extract to substantially enhance the feeding and growth rates of commercially farmed species such as trout, salmon and shrimp when added to the meal in concentrations useful in producing animal coloration. More particularly, this product induces growth rates substantially greater than any currently available food additive for aquaculture. Growth rates are especially enhanced for salmonid species such as salmon and trout and for shrimp. The economic impact of the ability to harvest fish and other animals such as shrimp much earlier is very meaningful in commercial aquaculture.

2. Description of the Related Art

Aquaculture is an increasingly important area of commerce around the world. Certain aquatic species derive flesh color from natural feeding sources. Such species as salmon, trout, koi, tropical fish, abalone, sea bream and crustaceans such as shrimp and lobster are the most common species which derive this natural pink color, astaxanthin, from the environment. However, when such species are commercially farmed, they no longer have access to this colorant and it is necessary to add it to the feed. It is known that addition of this material to the fish feed enhances the health and lowers the stress on the fish while also providing the necessary coloring of the flesh (Torrissen, O. J and Cristiansen, R., *J. Appl. Ichthyol*, 11, 225 (1995). Until recently, the only commercial sources of astaxanthin product were derived from total synthesis or the fermentation of *Pfaffia rhodozyma* yeast or growing of *Haematococcus* alga.

Recently, Breivik et al. (WO 03/003848) reported that the growth of Atlantic salmon was enhanced when the fish were fed an astaxanthin diester in combination with a concentrate comprising two different omega-3 fatty acids, compared to fish fed commercially available synthetic astaxanthin (Carophyll Pink, Roche). It should be noted that the maximum increase in growth after 15.5 months was only 9% above control. The inventors suggest that the diester form provides better growth rates in salmonid species than free unesterified astaxanthin.

SUMMARY OF THE INVENTION

In one aspect, the present invention relates to a method for enhancing feed consumption and growth rates for animal species, where the method includes the step of adding an astaxanthin product obtained from a marigold extract to the feed. Preferably, the animal is an aquatic animal such as a fish or crustacean. In a preferred embodiment, the aquatic animal is chosen from trout, salmon or shrimp.

The astaxanthin product is added to the feed in an amount sufficient to produce a concentration of astaxanthin product of between about 10 to 200 ppm. Preferably, the astaxanthin product is added to the feed in an amount sufficient to produce a concentration of astaxanthin product of between about 50 to 120 ppm. For some animals such as shrimp, the astaxanthin product may be added to the feed in an amount sufficient to produce a concentration of astaxanthin product of between about 20 to 30 ppm.

In some embodiments, the astaxanthin product may be obtained from the marigold extract by a process including the steps of treating the marigold extract with a strong base to isomerize lutein to zeaxanthin; and oxidizing the zeaxanthin to produce the astaxanthin product.

Preferably, the astaxanthin product which is added to the feed for enhanced feed consumption and growth rates of the animal species contains greater than 75% R.S. (meso) diastereomeric configuration. More preferably, the feed contains greater than 85% (meso) diasteriomeric configuration. In a most preferred embodiment, the astaxanthin product is present in the feed in a concentration greater than 90% R,S (meso) diastereomeric configuration. Preferably, the animal is an aquatic animal such as a fish or crustacean. More preferably, the aquatic animal is a trout a fish or a shrimp.

In a preferred embodiment, the astaxanthin product which contains the greater than 75%, 85% or 90% R,S (meso) diastereomeric configuration is added to the feed in an amount sufficient to produce a concentration of astaxanthin product of between about 10 to 200 ppm, preferably 50 to 120 ppm. In certain embodiments, such as supplying the astaxanthin product which contains the greater than 75%, 85% or 90% R,S (meso) diastereomeric configuration to certain animals such as shrimp a concentration of astaxanthin product of between about 20 to 30 ppm is preferred.

Further aspects, features and advantages of this invention will become apparent from the detailed description of the preferred embodiments which follow.

DETAILED DESCRIPTION OF THE PREFERRED EMBODIMENT

We have demonstrated a new, novel inexpensive source of astaxanthin product from the semi-synthetic conversion of marigold extract (lutein) to astaxanthin (Rodriguez, G. A., U.S. Pat. No. 5,973,211; Rodriguez, G. A., et al, U.S. Pat. No. 6,329,557; Schloemer, G. C. and J. L. Davis U.S. application Ser. No. 09/813,685 and Schloemer, G. C., et al, U.S. Pat. No. 6,372,946, all of which are incorporated herein by reference).

Preparation of Lutein and Zeaxanthin from Marigold Extracts

The preparation of lutein and zeaxanthin is described in U.S. Pat. No. 6,329,557, which is incorporated herein by reference. More specifically, the raw materials for this process include saponified marigold extracts containing 20 g/kg or more of green matter. In one preferred embodiment of the present invention, marigold extracts containing from about 40 to about 150 grams of carotenoids per kilogram and from about 5 to about 20 grams of chlorophyll per kilogram are used as starting materials. Such extracts are produced by Productos Deshidratados de Mexico (PRODEMEX), Los Mochis, Sinaloa, Mexico. The marigold flowers used for making these extracts may be mechanically harvested, having significant amounts of leaves, stems, peduncles and other plant parts rich in chlorophyll and derivatives.

Marigold meals are prepared by dehydrating the machine-harvested flowers. There are several ways of dehydrating, including belt, tray, shelf and drum dryers or sun drying. The dry material is milled and the process is followed by a solvent extraction using a non-polar solvent, such as for example, hexane. The solvent is then removed by evaporation and a marigold oleoresin is obtained. The oleoresin may then be saponified to complete hydrolysis of the xanthophylls and chlorophylls present. Saponification may be accomplished by treatment of the oleoresin with sodium or potassium hydroxide or some other alkali. The saponification conditions are well known to those of ordinary skill in the art.

Free lutein, zeaxanthin and other free xanthophylls are obtained during the saponification reaction, as well as sodium and potassium salts of fatty acids like myristic, palmitic and stearic acids. In addition, the phytyl and methyl groups on the pigment molecules may be substituted with sodium or potassium, depending on the base (e.g., NaOH or KOH, respectively) used as the saponifying agent. Water-soluble chlorophyllins may also be produced during saponification.

Isomerization of Lutein to Zeaxanthin

Lutein in the marigold oleoresin obtained above may be converted to zeaxanthin, essentially as taught by U.S. Pat. No. 5,973,211, which is incorporated herein by reference. Alkali and a glycol solution are added to the lutein-containing residue obtained above. The extract is homogenized in a glycol solution, such as propylene glycol, polyethylene glycol, glycerin, etc., using from 0.1 to 1 parts of glycol to 1 part of extract by weight. A mixture of glycols can also be used. The preferred reaction solvent is propylene glycol. A weight ratio of glycol to extract of 0.2 to 0.5 is also preferred.

A metal hydroxide, or a combination of alkaline reagents, is then added and the mixture is heated in a closed reaction vessel under nitrogen. When using a oleoresin extracted from machine harvested marigold flowers, a mixture of sodium hydroxide and potassium hydroxide is the preferred choice of alkaline reagents. Moreover, the amount of alkali required will vary, depending on the substrate and process conditions utilized. Generally, the total amount of metal hydroxide(s) is in the range of 0.1 to 0.4 parts per part of extract by weight.

The addition of the alkali can be done in two steps. First, enough metal hydroxide is added to achieve saponification of the extract. The quantity needed will depend on the saponification index of the extract which can be measured by a saponification number determination (adapted from AOAC Official Methods of Analysis, 15th ed., 920.160 (1990)). Generally, the stoichiometric amount is between 8% to 15% of alkali with respect to the weight of the extract.

The temperature used for saponification will depend on the material being saponified, and the saponification step can occur at a temperature lower than that used for the isomerization reaction which follows. The saponification step preferably occurs at a temperature between about 20° and about 180° C., more preferably between about 25° and 120° C., still more preferably between about 40° and about 100° C.

In a second step, more alkali can be added to effect the isomerization reaction. The amount of alkali required is usually within the range added for the saponification reaction. The alkali can be added in granular form or dispersed in the glycol used for the isomerization reaction.

The rate of the addition can vary, and greatly depends on the reactor mechanism for introduction of reactants. Moreover, when reactants are introduced, it is preferable not to disrupt the nitrogen blanket within the reactor by the introduction of air.

The time of reaction is variable, and largely depends on the actual temperature within the reactor. In general, the reactor is preferably operated between about 25° and about 180° C., with a reaction temperature from about 50° to about 150° C. being more preferred, temperatures between about 60° and about 120° C. being still more preferred, and a reaction temperature between about 80° and about 110° C. being even more preferred. Generally, the reactions of the present can be conducted using reaction times from about 30 minutes to 5 hours, or until the desired level of isomerization is achieved. The preferred reaction time is from about 3 to 5 hours. Of course, at higher reaction temperatures, the reaction time is shorter.

No additional pressure is required to be applied to the reactor when conducting the reactions of the present invention. The reaction pressure within the chamber is about 5 to 15 psi manometric, due mainly to the nitrogen blanket and the vapor pressure of the glycol solution. Additional pressure can be applied, however, if needed. The novel reactions can also be conducted under vacuum if desired.

The saponified and isomerized extract is dispersed in water and diluted to a final concentration of between about 0.1 to 30 grams of total xanthophylls per kilogram of the aqueous dispersion, preferably between about 5 to 10 grams per kilogram of aqueous dispersion as described in U.S. Pat. No. 6,329,557, incorporated herein by reference. Preferably, the aqueous dispersion is mixed thoroughly to form a homogeneous mixture.

The pH of the mixture is then adjusted to between about 1.0 to 7.0, and preferably, between about 5.0 to 6.5, using aqueous solutions of an acid selected from the group consisting of acetic, phosphoric, sulfuric, hydrochloric or any inorganic or organic acid having similar characteristics. The concentration of the acid solution can be fixed from about 5 to 25% (w/w). The temperature of the mixture should be kept between about 20° to 80° C., and preferably, between about 45° to 70° C. The pH of the mixture is sufficiently decreased (neutralized) when the aqueous phase, which contains the water-soluble chlorophyllins and other water-soluble impurities, separates readily from the upper oily residue. The lower aqueous phase can be withdrawn using a conventional separatory apparatus. The oily residue contains some residual water-soluble chlorophyllins and the xanthophylls.

Additional water washes maintaining a fixed pH, may be used to reduce the concentration of residual water-soluble green matter from the oily upper phase. For each wash, it is possible to use from between 4 to 20 volumes of water to residue, but preferably, between 8 to 15 volumes of water per volume of residue. The water washings may be pooled for subsequent isolation of the green pigments. Water washing may be continued until the oily residue is essentially free of chlorophylls and related compounds and contains mainly lipids, water and xanthophylls.

The humid oily residue is then extracted with a nonpolar solvent. The solvent may be selected from the group consisting of short chain aliphatic (e.g., hexane) or aromatic hydrocarbons, aLlcyl-substituted solvents or a mixture thereof. Preferably, the hydrocarbons have between 6 to 8 carbon atoms. For each part of oily residue, between about 1 to 20 parts of nonpolar solvent (w/w) may be used, and preferably, between about 5 to 10 parts (w/w) for each extraction. Preferably, at least two extractions are used. The extractions are done at a temperature of between about −20° and 70° C., preferably between about 15 °and 45° C., and more preferably between about 35° and 45° C. The lipids and carotenes, as well as other lipid-soluble substances, are extracted in the nonpolar solvent, which can be separated and pooled.

A solid that precipitates from the nonpolar solvent during the extraction is rich in lutein and zeaxanthin. Residual amounts of chlorophyll may still be present. One or two additional washes with a polar solvent should be sufficient to minimize the level of chlorophyll contamination. The polar solvent may be a ketone, alcohol, amine or any other polar solvent of similar nature. The solvent should be acidified using the same acid that was used for chlorophyllin separation. From 3 to 20 parts of solvent may be used relative to the weight of the residual solid but preferably between 6 to 10 parts. The washes are preferably conducted at ambient temperature. The solvent washes may be collected and the solvent recovered. Solvent is removed and the final solid is dried using conventional methods, preferably conducted under an inert atmosphere.

Preparation of Astaxanthin from Zeaxanthin

The conversion of zeaxanthin to astaxanthin is carried out essentially as described in U.S. Pat. No. 6,372,946, which is incorporated herein by reference. The zeaxanthin-containing residue obtained above is slurried in chloroform. In one embodiment of the invention, the ratio of zeaxanthin to organic solvent varies from 1:10 to 1:500 depending upon the reaction conditions. Preferably, the ratio of zeaxanthin to the organic solvent is from about 1:10 to about 1:200. The pH is acidic and preferably the pH is 1-3.

To this mixture is added the oxidizing agent which is formed from a solution of sodium bromate to which an aqueous solution of sodium metabisulfite is added dropwise over three hours at temperatures between 20 to 30° C. The ratio of oxidizing agent relative to zeaxanthin can vary between a catalytic amount to 2 molar equivalents. The term "catalytic amount" refers to an amount of the oxidizing agent that is less than the stoichiometric quantity of the zeaxanthin used in the reaction. The term "stoichiometric" refers to the use of an equivalent mole ratio or amount of a reagent relative to a selected substrate, molecule or compound in the reaction.

After addition, the reaction mixture is filtered through Celite and the aqueous phase is separated. The chloroform is removed by vacuum evaporation at 40-42° C. The resulting slightly wet solid is added to warm (50° C.) 95% ethanol. The mixture is stirred and cooled slowly to −10° C. The resulting solid is filtered off and dried under vacuum.

Use of Astaxanthin Additive in Aquaculture

Feeding studies in several locations have indicated remarkable and unexpected enhancement in the feeding and growth rates for fish and other aquatic species fed with similarly prepared meal but with the astaxanthin additive of the present invention compared with other commercially available additives. In fact, we have observed a growth rate enhanced of around 40% which clearly would have major economic benefits for anyone involved in aquaculture.

The ability to grow and harvest fish and other aquatic species such as shrimp faster has major economic benefits for anyone involved in aquaculture. More weight of fish or shrimp per time frame means enhanced use of capital resources and thus lower cost of production. Therefore, any additive that can economically be added to the feed to enhance feeding and growth rates would be highly desirable. We have now derived such an additive which can produce the dual role of fish or shrimp coloration and substantial growth enhancement in an economical manner. Although the invention is described with reference to salmon, trout, and shrimp, it is understood that the astaxanthin additive described herein may be useful as a feed supplement in many commercially farmed products including, but not limited to, salmon, trout, koi, tropical fish, abalone, shrimp, and sea bream.

Astaxanthin additives have been used in the salmon and trout aquaculture industry to produce flesh coloration resulting in a more desirable fish in the marketplace. The cost of obtaining this coloration is substantial and the addition of this material to the feed has a significant economic impact. Recently, we have demonstrated a novel method of obtaining an astaxanthin product by semi-synthesis from lutein which was derived from marigold extract. The lutein is first converted to zeaxanthin by known technology and finally to astaxanthin product by oxidation (as described above). Various concentrations of astaxanthin in our product have been tested in several studies for flesh coloration. While these studies indicated excellent flesh coloration, they also all indicated remarkably enhanced growth rates for our fish fed our additive versus fish fed the leading commercially available additive. It was determined that fish fed the commercially available additive would stop eating at a point much earlier than fish fed food containing similar concentrations of our additive. The difference is remarkable and substantial with growth rate enhancements of around 40% observed. Clearly this has major economic benefits in the industry.

While it is not known exactly why fish consume substantially more feed containing marigold-derived additive, there are some clear differences in the composition. First, residual sugars and proteins and other substances derived from the marigold flower extract are present in our additive. These may have the effect of enhancing the feeding rates of the fish. Secondly, our astaxanthin product differs from those presently available in that we have substantially pure R,S-meso diasteriomers (>90%) while the synthetic material is a mixture of R,R and S,S and R,S diasteriomers. The naturally derived astaxanthin product from algae and from yeast contains predominately the R,R or S,S diasteriomer. Therefore, our product is unique in this regard. This also may contribute to the enhanced feeding observed. The additive is derived by the following scheme.

REACTION SCHEME

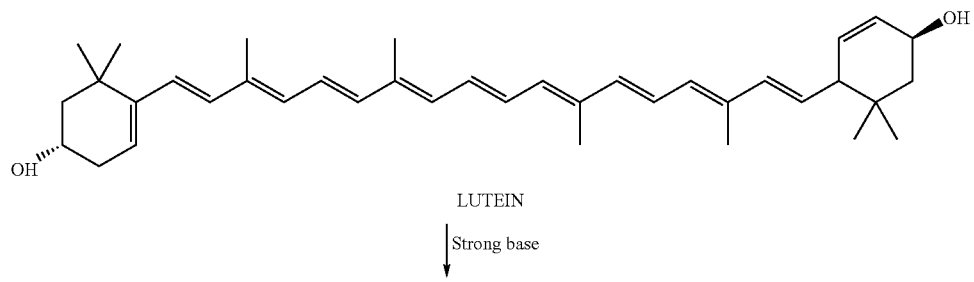

LUTEIN

Strong base

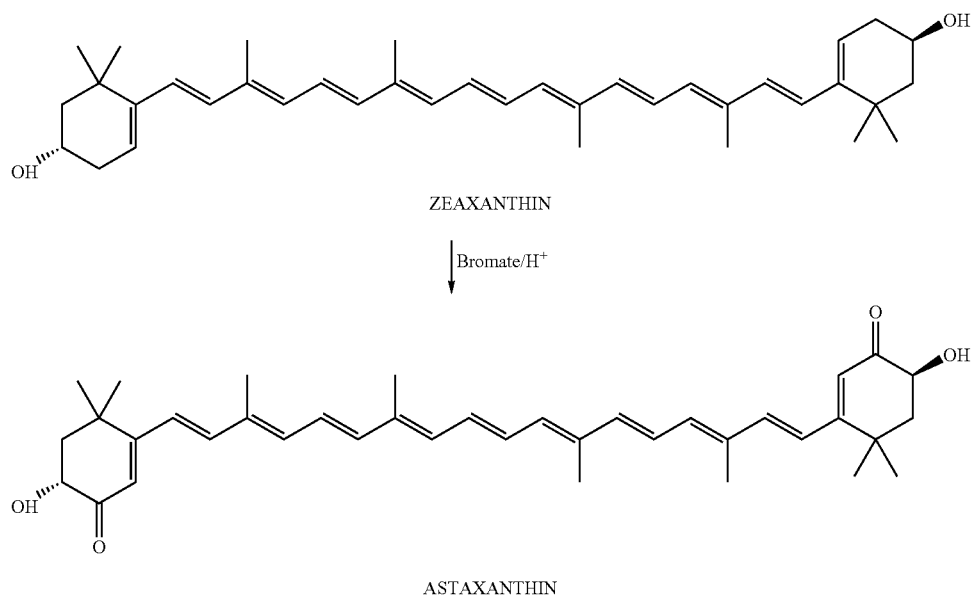

ZEAXANTHIN

↓ Bromate/H⁺

ASTAXANTHIN

WORKING EXAMPLES

Example 1

Rainbow trout of an approximate average weight of 132 g were weighed and placed into fifteen 150l tanks supplied with 6l/min untreated, 14.5° C. spring water placing 35 fish in each tank. The fish were fed ad lib during a period of 15 weeks. Total feed consumed for each treatment was measured. The fish were grouped into five different treatments with three replicates for each. Three of the treatments received feed with inclusion of astaxanthin derived from marigold extract and the other two treatments were used as controls. One of the controls had synthetic astaxanthin added and the other control had no astaxanthin of any source.

Throughout the experiment 9 fish were sacrificed from each replicate of each treatment for growth and pigmentation measurements. Weights, feed and conversion ratios are summarized in Table 1 for this experiment. Feed Conversion Ratio (F.C.R.) is used in its usual meaning which is defined as the amount of feed added/amount of product obtained.

In the treatments with astaxanthin derived from marigolds (FLORAFIL-AX™) a weight gain of more than 46% was obtained compared to the controls. Also in the FLORAFIL-AX™ treatments the average end weight was over 500 grams while in the control treatments approximately 400 grams were obtained. The fish in the FLORAFIL-AX™ treatments ate much more consuming over 40 kg of feed compared to less than 30 kg in the controls. The feed conversion ratio was also better in the FLORAFIL-AX™ treatments with an overall average of 1.61 compared to 1.75 in the control treatments.

Example 2

A field trial with Rainbow Trout was done to assess pigmentation and growth in a commercial fish farm. The fish were grown in concrete raceways where fish were stocked in two sections of different raceways. In one section we had the control treatment which was fed with feed containing synthetic astaxanthin at 90 ppm. The other raceway had a treatment with feed containing 90 ppm of astaxanthin derived from lutein from marigold extract. The water tem-

TABLE 1

DATA FOR WEIGHTS, FEED CONSUMED AND FEED CONVERSION RATIOS IN EXPERIMENTAL TRIAL WITH RAINBOW TROUT (Weights are in kg)

| Diet | # of fish at Start | # of fish at end | Total Start Wt. | Total End Wt. | Total Wt Gain | Avg Start Wt. | Avg End Wt. | Avg Wt Gain | Total Feed | F.C.R. |
|---|---|---|---|---|---|---|---|---|---|---|
| Control 1 | 105 | 78 | 13.896 | 31.461 | 17.565 | 0.132 | 0.403 | 0.271 | 29.694 | 1.73 |
| Florafil AX-1 | 105 | 78 | 13.941 | 40.839 | 26.901 | 0.133 | 0.524 | 0.391 | 43.569 | 1.62 |
| Florafil AX-2 | 105 | 78 | 14.049 | 40350 | 26.301 | 0.134 | 0.517 | 0.384 | 41.478 | 1.58 |
| Florafil AX-3 | 105 | 78 | 13.503 | 40.449 | 26.946 | 0.129 | 0.519 | 0.390 | 44.103 | 1.64 |
| Control 2 | 105 | 78 | 14.070 | 30.576 | 16.506 | 0.134 | 0.392 | 0.258 | 29.043 | 1.77 | perature was constant at 16° C. throughout the test as was the flow rate at 60 1/sec. Fish were fed to satiate, feed consumed was weighed for each treatment and conversion rates calculated based on the initial and final biomass. Table 2 presents the data for this trial.

TABLE 2

GROWTH AND CONVERSION DATA FOR FIELD TRIAL ON RAINBOW TROUT IN A COMMERCIAL FISH FARM (Weights are in kg)

| Treatment | # of fish at start | Initial Biomass | # of fish at end | Final Biomass | Feed consumed | Conv. Ratio | Average Initial Wt | Average end Wt | Average Wt gain |
|---|---|---|---|---|---|---|---|---|---|
| Synthetic astaxanthin | 500 | 74.5 | 459 | 154.6 | 125.2 | 1.56 | 0.149 | 0.337 | 0.188 |
| Marigold Derived astaxanthin | 500 | 76.1 | 467 | 236.7 | 245.0 | 1.52 | 0.152 | 0.507 | 0.355 |

Results clearly show that the fish with feed containing astaxanthin product derived from marigold extract eat much more. It is evident that this feed enhances ingestion and consequently growth as manifested by the body weight. At the end of the feeding trial, the average weight gain was enhanced by 88.8% in the marigold-derived (355 grams) vs. synthetic (188 grams) astaxanthin groups. Conversion ratios were found to be very similar.

Example 3

Penaeid shrimp (*Litopenaeus vannamei*) with an average initial weight of 0.96 gr were stocked at a density of 25.04 individuals/square meter in four different culture ponds. There were three ponds for each treatment to give a total of 12 ponds. The size of the ponds differed slightly as shown in Table 3 where a summary of the yields obtained after harvesting are also presented. All ponds were fed with the same diets varying only in the type of pigment used and keeping one as a control without pigment addition. Weight of feed supplied to each pond was recorded daily and the feed conversion ratio calculated after harvesting. Culture of the shrimp was done following normal commercial procedures and doing exactly the same operations in all ponds. After harvesting the only treatment that had a higher production compared to the control was the one with marigold derived astaxanthin included in the diet. The treatments with the synthetic astaxanthin and high zeaxanthin had a low survival rate.

Those skilled in the art will appreciate that numerous changes and modifications may be made to the preferred embodiments of the invention and that such changes and modifications may be made without departing from the spirit of the invention disclosed herein. It is therefore intended that the appended claims cover such equivalent variations as may fall within the true spirit and scope of the invention.

What is claimed is:

1. A method for enhancing feed consumption and growth rates for aquatic animals comprising obtaining an astaxanthin product from a marigold extract by treating the marigold extract with a strong base to isomerizes lutein to zeaxanthin, and oxidizing the zeaxanthin to produce the astaxanthin product, and then adding the asstaxanthin product obtained from the marigold extract to aquatic animal food.

2. The method of claim 1, wherein the aquatic animal is a fish or crustacean.

3. The method of claim 2, wherein the fish is selected from the group consisting of trout or salmon.

4. The method of claim 2, wherein the crustacean is shrimp.

5. The method of claim 1, wherein the astaxanthin product is added to the feed in an amount sufficient to produce a concentration of astaxanthin product of between about 10 to 200 ppm.

6. The method of claim 5, wherein the astaxanthin product is added to the feed in an amount sufficient to produce a concentration of astaxanthin product of between about 50 to 120 ppm.

TABLE 3

FIELD TRIAL ON A COMMERCIAL SHRIMP FARM USING SEVERAL PIGMENT SOURCES TO EVALUATE PRODUCTION

| | | | HARVEST | | | |
|---|---|---|---|---|---|---|
| FEED | SURFACE (Hectares) | REARING TIME (Days) | % Survival | Kg | Kg/Hect | Feed Conv Ratio |
| With Marigold derived astaxanthin (25 ppm) | 15.8 | 100 | 75.4 | 35,067 | 2,219 | 1.43 |
| With pigment high in Zeaxanthin (80 ppm) | 12.6 | 96 | 58.5 | 20,515 | 1,628 | 1.80 |
| With synthetic astaxanthin (25 ppm) | 14.6 | 92 | 66.5 | 18,729 | 1,283 | 1.62 |
| Without pigment added | 13.7 | 98 | 72.8 | 28,125 | 2,053 | 1.50 |

7. The method of claim 5, wherein the astaxanthin product is added to the feed in an amount sufficient to produce a concentration of astaxanthin product of between about 20 to 30 ppm.

8. A method for enhancing feed consumption and growth rates for aquatic animal species, comprising obtaining an astaxanthin product which comprises greater than 90% R, S (meso) diastereomeric configuration from a marigold extract and then adding the astaxanthin product obtained from the mairogold extract to aquatic animal food.

9. The method of claim 8, wherein the aquatic animal is a fish or crustacean.

10. The method of claim 9, wherein the fish is selected from the group consisting of trout or salmon.

11. The method of claim 9, wherein the crustacean is shrimp.

12. The method of claim 8, wherein the astaxanthin product is added to the feed in an amount sufficient to produce a concentration of astaxanthin product of between about 10 to 200 ppm.

13. The method of claim 12, wherein the astaxanthin product is added to the feed in an amount sufficient to produce a concentration of astaxanthin product of between about 50 to 120 ppm.

14. The method of claim 11, wherein the astaxanthin product is added to the feed in an amount sufficient to produce a concentration of astaxanthin product of between about 20 to 30 ppm.

* * * * *